United States Patent [19]

Tsang et al.

[11] 4,415,676
[45] Nov. 15, 1983

[54] SYNGAS CONVERSION PROCESS

[75] Inventors: Wen-Ghih Tsang, Framingham, Mass.; Lynn H. Slaugh, Cypress, Tex.

[73] Assignee: Shell Oil Company, Houston, Tex.

[21] Appl. No.: 410,297

[22] Filed: Aug. 23, 1982

[51] Int. Cl.³ .............................................. C07C 1/04
[52] U.S. Cl. .................................................... 518/715
[58] Field of Search ........................................ 518/715

[56] References Cited

U.S. PATENT DOCUMENTS 4,157,338  6/1979  Haag et al. .................... 518/715

*Primary Examiner*—Howard T. Mars

[57] ABSTRACT

A process for converting syngas to $C_{25}$–$C_{30}$ paraffins which process comprises contacting the syngas with a catalyst comprising ruthenium metal on a faujasite type of zeolite which is subsequently treated with a borane solution and calcined under special conditions is disclosed herein.

3 Claims, No Drawings

SYNGAS CONVERSION PROCESS

FIELD OF THE INVENTION

This invention relates to a process for converting syngas to paraffins having a carbon number range of about 27–33 utilizing a ruthenium-based catalyst.

BACKGROUND OF THE INVENTION

Narrow range paraffins having carbon numbers around 30 can provide commercially useful compounds. For example, $C_{30}$ paraffins can be added to candle waxes to impart special properties. They can be converted to other useful products such as chloro-paraffins, olefins, alcohols, acids, amines, etc. Recently, 1-triacontanol has been reported as having plant growth regulating activity.

SUMMARY OF THE INVENTION

The instant invention relates to a process for converting syngas to paraffins with carbon numbers ranging from about 25 to about 35 which process comprises contacting the syngas with a catalyst composition prepared by ion exchanging a ruthenium-containing solution with a faujasite type zeolite, calcining and then reducing the ruthenium-containing zeolite, subsequently contacting the ruthenium-containing zeolite with borane, and subsequently calcining in air and then reducing the borane-treated material. The use of catalyst compositions prepared in this fashion produces a narrow range of paraffins centered around $C_{30}$. The instant catalysts also differ significantly from similar catalysts described in applicants' copending application Ser. No. 410,232, filed Aug. 23, 1982, wherein the catalyst is calcined in nitrogen rather then air just prior to the final reduction.

DESCRIPTION OF THE PREFERRED EMBODIMENTS

The instant invention comprises a process for converting a mixture of carbon monoxide and hydrogen (syngas) to a hydrocarbon product which comprises a narrow range of paraffins, centered around $C_{30}$ and generally having carbon numbers ranging from about 25 to about 35, preferably from about 27 to about 33. This process comprises contacting the syngas with a catalyst composition prepared by:

a. ion-exchanging the sodium ions of the sodium form of the faujasite type zeolite with ruthenium ions by contacting said zeolite with a solution containing a soluble ruthenium compound, b. calcining the ruthenium exchanged zeolite in nitrogen at a temperature ranging from about 300° C. to about 600° C.

c. contacting the ruthenium-containing zeolite with hydrogen at a temperature ranging from about 300° C. to about 600° C. whereby the ruthenium is reduced to the metal, d. contacting the ruthenium metal-containing zeolite with a solution of borane, e. calcining the borane-treated zeolite in air at a temperature ranging from about 300° C. to about 600° C. and then f. contacting the borane-treated zeolite with hydrogen at a temperature ranging from about 300° C. to about 600° C.

The zeolite used to prepare the catalysts used in the instant invention is of the faujasite type and is utilized initially in the sodium form, that is, the various exchange sites are satisfied by sodium. Such zeolites are described in U.S. Pat. Nos. 2,882,244, usually referred to as X zeolite and 3,216,789, referred to as a Y zeolite, and also in 3,446,727. These faujasitic type zeolites have been widely employed in catalytic processes such as for the conversion of hydrocarbons and are generally well known. The patent and general literature are extensive on these. In preparing the instant compositions, the sodium form of the faujasite type zeolite is contacted with a solution of a ruthenium salt whereby the ruthenium ion is ion-exchanged with the sodium ion. Any suitable, soluble ruthenium salt can be utilized, dissolved in an appropriate solvent. Suitable salts and solvents are readily determined by one skilled in the art. Illustrative examples of suitable ruthenium salts include salts such as ruthenium (III) chloride hydrate, ruthenium (III) bromide, anhydrous ruthenium (III) chloride and ruthenium nitrate. Also suitable are the ammonia complexes of the ruthenium halide such as, for example, $Ru(NH_3)_6Cl_3$ and $Ru(NH_3)_6I_3$. Salts of suitable organic acids are also suitable. Here, examples include ruthenium (III) acetate, ruthenium (III) propionate, ruthenium hexafluoracetylacetonate, ruthenium (III) triofluoracetate, ruthenium octanoate, ruthenium naphthenate, ruthenium valerate, and ruthenium (III) acetylacetoneate.

Suitable solvents for the desired ruthenium compounds can readily be determined by simple experimentation. Preferred solvents are water and the lower alkanols. After contacting the sodium form of the zeolite with the ruthenium-containing solution, the ruthenium-exchanged zeolite is dried and then calcined in nitrogen at a temperature ranging from about 300° C. to about 600° C. Calcination times are not critical and range from about 0.1 to about 20 hours. After calcination, the ruthenium-containing zeolite is reduced in a hydrogen atmosphere at a temperature ranging from about 300° C. to about 600° C. The reaction time is not critical but is adjusted according to the temperature of reduction, higher reduction temperatures will require shorter times and vice versa. Generally, times range from about 0.1 to about 20 hours. The reduction conditions are chosen, such as to reduce the ruthenium which is an ionic form in the zeolite to ruthenium metal which will be deposited on the surfaces (external and pore volume) of the zeolite.

The ruthenium metal-containing zeolite is then contacted with a solution of barane ($BH_3$ or diborane $B_2H_6$) in a suitable organic solvent. Suitable solvents comprise the ether solvents, particularly suitable is tetrahydrofuran. The borane is typically prepared by the reaction of a metal hydride with a boron halide in an ether-type solvent. The borane compounds are sensitive to both air and moisture, so the above mentioned impregnation of the zeolite with the borane compound must be maintained under anhydrous, air-free conditions.

After the zeolite has been impregnated with the borane solution, it is dried at relatively low temperatures up to about 50° C., and then calcined in air at a temperature ranging from about 300° C. to about 600° C. The calcined borane-treated zeolite is then reduced in a hydrogen atmosphere at a temperature ranging from about 300° C. to about 600° C. Calcination and reduction times are not critical and range from about 0.1 to about 20 hours.

The resultant catalytic material is used in a fashion typical of that utilized for heterogeneous catalysts. It may be used in fixed beds, in fluidized beds or in batch reactors. Typical reaction temperatures range from about 175° C. to about 350° C., preferably from about 200° C. to about 300° C. Typical reaction pressures range from about 5 to about 500 bar, preferably from about 5 to about 200 bar, and typical feed rates include gaseous hourly space velocities ranging from about 500 to about 10,000 l/l/hour. A wide range of carbon monoxide to hydrogen can be used in the feed. For example, a $CO:H_2$ ratio ranging from about 1:2 to about 3:1 is generally suitable.

The product of the instant process comprises a large portion of paraffins having a narrow range of carbon numbers. Generally, about 70 percent or greater by weight of the product will be paraffins having carbon numbers ranging between about 25 and about 35, preferably between about 27 to about 33.

The process of the instant invention, including preparation of the catalyst composition, will be further described below by the following illustrative embodiments which are provided for illustration and are not to be construed as limiting the invention.

ILLUSTRATIVE EMBODIMENTS

Catalyst Preparation

The following example illustrates the typical preparation of a composition falling within the scope of the instant invention. 30 Grams of $Ru(NH_3)_6Cl_3$ are dissolved in 150 cc of water and added to a 50 cc condensing flask. 60 Milliliters of the soidum form of Y zeolite (L24-52/RW Linde) was calcined for 24 hours at 500° C. and then added to the reflux flask and refluxed for about two hours. The zeolite was then filtered and washed with approximately 500 cc of water. The zeolite was then placed in a quartz flow tube and calcined in a nitrogen flow (at about 550° C. for about five hours). The temperature was raised from room temperature to 550° C. at a rate of approximately 10° C. per minute. After calcining, the quartz flow tube was cooled and the hydrogen flow was initiated through the tube. The temperature was then again raised to about 500° C. at a rate of about 10° C. per minute. The material was maintained at 500° C. for about two hours. After reduction the sample was cooled to room temperature. Twenty-five cubic centimeters of the ruthenium-treated zeolite was contacted with 125 cc of a one molar solution of $BH_3$ in tetrahydrofuran. The borane-treated material was then dried at about 40° C. on a rotovac dryer for about three hours. The sample was then placed in a quartz tube, air flow was initiated and the tube was heated at about 10° C. per minute to about 550° C. for about five hours. After calcination the sample was cooled, hydrogen flow was then initiated over the sample, and the sample was heated to about 500° C. at a rate of about 10° C. per minute for about two hours. After this reduction, the sample was cooled overnight. During the above preparative techniques, the sample was maintained under dry box conditions except for the calcination and reduction process.

PROCESS

Syngas Reaction

The catalyst composition, according to this invention (Example 1), was prepared in the fashion described above. Analysis of this composition showed that it had approximately 7.1% w ruthenium and about 1.2% w boron. The sample was placed in a tubular flow reactor and heated to the appropriate reaction temperature as indicated in Table 1. Carbon monoxide and hydrogen in a molar ratio of about 1:1 were fed to the reactor under the conditions indicated in Table 1. The products of the reactor were analyzed by gas chromatography and $C^{13}$ nuclear magnetic resonance, and the results are shown in Table 1 below. Greater than about 70 weight percent of the products are paraffins within the $C^{25}$-$C^{35}$ range, with the average carbon number around 30. For comparative purposes, other compositions not falling within the scope of this invention were prepared. Example A comprises a composition prepared according to the teachings of applicants' copending application Ser. No. 410,298, filed Aug. 23, 1982, wherein just prior to the final reduction the composition is calcined in nitrogen, rather than air. Example B comprises a ruthenium metal supported on a Y zeolite. This is basically the same as Example 1 without the borane treatment. Example C comprises the use of an alumina-silica as a support rather than a zeolite. The alumina-silica is Davison 980-25 which has a similar Al/Si ratio as the Y zeolite. This example was prepared in the same fashion as Example 1 except without the borane treatment. As can be seen from the table, the composition of the instant invention provides a high selectivity to paraffins with carbon numbers around 30, as compared to the other examples which provide lower paraffins, olefins and oxygenates.

TABLE 1

| SYNGAS CONVERSIONS BY RU/B/Y AND RELATED CATALYSTS | | | | |
|---|---|---|---|---|
| Example: | 1 | A | B | C |
| Catalyst: | Ru/B/Y | Ru/B/Y | Ru/Y | Ru/Al-Si* |
| Ru (% w) | 7.10 | 6.00 | 7.10 | 3.96 |
| B (% w) | 1.02 | 0.97 | — | — |
| GHSV (l/l/hr) | 4300 | 4000 | 4000 | 4000 |
| Temperature (°C.) | 250 | 250 | 220 | 250 |
| Pressure (psig) | 1000–1500 | 1500 | 1800 | 1500 |
| % Syngas (1:1) Conversion | 15.5 | 6.4 | 5.1 | 2.8 |
| Molar Selectivity % | | | | |
| $C_1$ Methane | 3.2 | 20.6 | 12.8 | 22.6 |
| Methanol | 0.4 | 3.8 | 0.6 | 0.78 |
| $C_2$ Ethylene/Ethane | 1.5/— | 2.4/— | 4.0/0.6 | 7.1/— |
| Ethanol | — | 1.8 | — | — |
| $C_3$ Propene/Propane | —/— | 0.3/2.4 | 1.1/2.2 | —/4.1 |
| Propanol | — | — | — | — |
| $C_4$ Butene/Butane | —/2.9 | 2.0/8.8 | —/11.7 | 3.4/14.2 |
| Butanol | — | — | — | — |
| In $C_5^+$ | | | | |
| $C_5^+$ | 91.0 | 57.9 | 67.2 | 46.9 |

TABLE 1-continued

SYNGAS CONVERSIONS BY RU/B/Y AND RELATED CATALYSTS

| Example: | 1 | A | B | C |
|---|---|---|---|---|
| Catalyst: | Ru/B/Y | Ru/B/Y | Ru/Y | Ru/Al-Si* |
| Paraffins | about $C^{30}$ | 41.4 | 54.7 | 50.7 |
| Olefins | paraffins | 16.4 | 31.0 | 31.2 |
| Alcohols | ↓ | 24.6 | 5.5 | 10.6 |
| Aldehydes | ↓ | 11.9 | 3.2 | 6.7 |
| Overall | | | | |
| Paraffins | ↓ | 57.5 | 64.0 | 64.6 |
| Olefins | ↓ | 14.2 | 25.7 | 25.1 |
| Alcohols | ↓ | 19.8 | 4.4 | 5.8 |
| Aldehydes | ↓ | 6.9 | 2.2 | 3.1 |

*Davison 980-25 alumina-silicate which has similar Al/Si ratio as Y zeolite.

We claim:

1. A process for converting a mixture of hydrogen and carbon monoxide to a hydrocarbon product which comprises 70 or more weight percent of paraffins having carbon numbers between about 25 and about 35 which process comprises contacting the hydrogen and carbon monoxide at a temperature ranging from about 175° C. to about 350° C. and a pressure ranging from about 5 bar to about 500 bar with a catalyst composition prepared by a process which comprises:
   a. ion-exchanging the sodium ions of the sodium form of a faujasite type zeolite with ruthenium ions by contacting said zeolite with a solution containing a soluble ruthenium comound,
   b. calcining the ruthenium exchanged zeolite in nitrogen at a temperature ranging from about 300° C. to about 600° C.,
   c. contacting the ruthenium-containing zeolite with hydrogen at a temperature ranging from about 300° C. to about 600° C. whereby the ruthenium is reduced to the metal,
   d. contacting the ruthenium metal-containing zeolite with a solution of borane,
   e. calcining the borane-treated zeolite in air at a temperature ranging from about 300° C. to about 600° C. and then
   f. contacting the borane-treated zeolite with hydrogen at a temperature ranging from about 300° C. to about 600° C.

2. The process of claim 1 wherein preparing the catalyst composition in an aqueous solution of $Ru(NH_3)_6Cl_3$ is used in step a. and a tetrahydrofuran solution of borane is used in step d.

3. The process of claim 1 or 2 wherein the paraffin product has carbon numbers ranging from about 27 to about 33.

* * * * *